United States Patent
Ghosh et al.

(10) Patent No.: US 7,259,133 B2
(45) Date of Patent: *Aug. 21, 2007

(54) FABRIC CARE COMPOSITIONS FOR LIPOPHILIC FLUID SYSTEMS CONTAINING AN ANTIMICROBIAL AGENT

(75) Inventors: Chanchal Kumar Ghosh, West Chester, OH (US); John Christian Haught, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 452 days.

This patent is subject to a terminal disclaimer.

(21) Appl. No.: 10/877,549

(22) Filed: Jun. 25, 2004

(65) Prior Publication Data

US 2004/0261195 A1 Dec. 30, 2004

Related U.S. Application Data

(60) Provisional application No. 60/482,955, filed on Jun. 27, 2003.

(51) Int. Cl.
*C11D 7/50* (2006.01)
(52) U.S. Cl. .................... 510/286; 68/12.08
(58) Field of Classification Search ............. 510/286; 68/12.08
See application file for complete search history.

(56) References Cited

U.S. PATENT DOCUMENTS

| 3,697,220 A | 10/1972 | Schwartz |
| 4,406,809 A | 9/1983 | Hasenclever |
| 5,942,007 A | 8/1999 | Berndt et al. |
| 6,894,014 B2* | 5/2005 | Deak et al. ............. 510/285 |
| 2002/0007519 A1* | 1/2002 | Noyes et al. ............. 8/137 |

FOREIGN PATENT DOCUMENTS

| DE | 2 010 809 | 9/1971 |
| GB | 1 067 064 A | 5/1967 |
| WO | WO 01/94678 A1 * | 12/2001 |
| WO | WO 03/000833 A1 | 1/2003 |
| WO | WO 03/006733 A1 | 1/2003 |
| WO | WO 03/008698 A1 | 1/2003 |

* cited by examiner

*Primary Examiner*—John R. Hardee
(74) *Attorney, Agent, or Firm*—Kim William Zerby; Steven W. Miller

(57) ABSTRACT

Compositions for treating fabric articles, especially articles of clothing, linens and drapery, wherein the compositions provide improved cleaning of soils from and/or care of and/or treatment of fabric articles, especially while providing an antimicrobial agent.

1 Claim, 2 Drawing Sheets

FABRIC CARE COMPOSITIONS FOR LIPOPHILIC FLUID SYSTEMS CONTAINING AN ANTIMICROBIAL AGENT

CROSS-REFERENCE TO RELATED APPLICATIONS

This application claims priority under 37 U.S.C. § 119(e) to U.S. Provisional Application Ser. No. 60/482,955, filed Jun. 27, 2003.

FIELD OF THE INVENTION

The present invention relates to methods for administering an antimicrobial agent to a laundering device for treating fabric articles, especially articles of clothing, linens and drapery, wherein the antimicrobial agent provides improved cleaning and/or care of and/or treatment of fabric articles.

BACKGROUND OF THE INVENTION

For the cleaning of fabric articles consumers currently have the choice of conventional laundry cleaning or dry cleaning.

Conventional laundry cleaning is carried out with relatively large amounts of water, typically in a washing machine at the consumer's home, or in a dedicated place such as a coin laundry. Although washing machines and laundry detergents have become quite sophisticated, the conventional laundry process still exposes the fabric articles to a risk of dye transfer and shrinkage. Significant portions of fabric articles used by consumers are not suitable for cleaning in a conventional laundry process. Even fabric articles that are considered "washing machine safe" frequently come out of the laundry process badly wrinkled and require ironing.

Dry cleaning processes rely on non-aqueous solvents for cleaning. By avoiding water these processes minimize the risk of shrinkage and wrinkling; however, cleaning of soils, particularly water-based and alcohol-based soils, is very limited with these processes. Typically, the dry-cleaner removes such soils by hand prior to the dry-cleaning process. These methods are complex, requiring a wide range of compositions to address the variety of stains encountered, very labor intensive and often result in some localized damage to the treated article.

Non-aqueous washing technologies are now emerging for home use. These technologies typically involve the use of a specialized laundering device equipped to utilize various solvents. An example of such washing technologies is illustrated in U.S. Patent Application Publication No. US 2002/0133886 to Severns et al. In order to obtain the most thorough cleaning, these technologies use various compositions for cleaning.

When dealing with any cleaning process, microbes and microbe concentrations are extremely important. The presence of microbes can cause cleaning results that are unsatisfactory. For instance, microbial infestations in fabric cleaning can result in fabric articles having an unpleasant odor or discoloration.

Non-aqueous washing techniques have many areas where microbial contamination could become problematic. Accordingly there is an unmet need providing antimicrobial agents to laundering devices and compositions for non-aqueous washing.

SUMMARY OF THE INVENTION

The present invention includes a method of treating microbes in a non-aqueous laundering process comprising
a) Laundering fabric articles by a non-aqueous laundering process using a lipophilic fluid,
b) Introducing an antimicrobial agent to the non-aqueous laundering process,
c) Reducing the effectiveness of the microbes with the antimicrobial agent, and
d) Optionally removing the microbes from cleaning composition.

These and other aspects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All measurements are in SI units unless otherwise specified. All documents cited are, in relevant part, incorporated herein by reference.

DETAILED DESCRIPTION OF THE INVENTION

Definitions

The term "fabric article" used herein is intended to mean any article that is customarily cleaned in a conventional laundry process or in a dry cleaning process. As such, the term encompasses articles of clothing, linens, drapery, and clothing accessories. The term also encompasses other items made in whole or in part of fabric, such as tote bags, furniture covers, tarpaulins and the like.

The term "fabric article treating composition" used herein is intended to mean any lipophilic fluid-containing composition containing cleaning and/or care additives that comes into direct contact with fabric articles to be cleaned. It should be understood that the term "fabric article treating composition" encompasses uses other than cleaning, such as conditioning and sizing. Furthermore, optional cleaning adjuncts such as additional surfactants other than those surfactants described above, bleaches, and the like may be added to the "fabric article treating composition". That is, cleaning adjuncts may be optionally combined with the lipophilic fluid. These optional cleaning adjuncts are described in more detail hereinbelow. Such cleaning adjuncts may be present in the fabric article treating compositions of the present invention at a level of from about 0.01% to about 10% by weight of the fabric article treating composition.

The term "soil" means any undesirable substance on a fabric article that is desired to be removed. By the terms "water-based" or "hydrophilic" soils, it is meant that the soil comprised water at the time it first came in contact with the fabric article, or the soil retains a significant portion of water on the fabric article. Examples of water-based soils include, but are not limited to, beverages, many food soils, water soluble dyes, bodily fluids such as sweat, urine or blood, and outdoor soils such as grass stains and mud.

The term "capable of suspending water in a lipophilic fluid" means that a material is able to suspend, solvate and/or emulsify water, in a way that the water remains visibly suspended, solvated or emulsified when left undisturbed for a period of at least five minutes after initial mixing of the components. In some examples of compositions in accordance with the present invention, the compositions may be colloidal in nature and/or appear milky. In other examples of compositions in accordance with the present invention, the compositions may be transparent.

The term "insoluble in a lipophilic fluid" means that when added to a lipophilic fluid, a material physically separates from the lipophilic fluid (i.e. settle-out, flocculate, float) within 5 minutes after addition, whereas a material that is "soluble in a lipophilic fluid" does not physically separate from the lipophilic fluid within 5 minutes after addition.

The term "consumable detergent composition" means any detersive composition, that when combined with a discrete lipophilic fluid, results in a fabric article treating composition according to the present invention.

The term "processing aid" refers to any material that renders the consumable detergent composition more suitable for formulation, stability, and/or dilution with a lipophilic fluid to form a fabric article treating composition in accordance with the present invention.

The term "mixing" as used herein means combining two or more materials (i.e., more specifically a discrete lipophilic fluid and a detergent composition in accordance with the present invention) in such a way that a homogeneous mixture or stable dispersion or suspension is formed. Suitable mixing processes are known in the art. Nonlimiting examples of suitable mixing processes include vortex mixing processes and static mixing processes.

"Solvent compatibility group", as used herein, means any hydrocarbon, silicone, polyalkylene oxide (ethoxy, propoxy, butoxy, etc. and mixtures) or flurorinated groups. Hydrocarbon groups may be linear, cyclic, branched, saturated or unsaturated straight and branched chain linear aliphatic; saturated and unsaturated cyclic aliphatic, including heterocyclic aliphatic; or mononuclear or polynuclear aromatics, including heterocyclic aromatics. Polyoxyalkylene groups may comprise of one or more or a mixture of alkoxy repeat units. Silicone and fluorinated groups may consist of one or more or a mixture of repeat units.

"Functionalized", as used herein, means the indicated solvent compatibility groups are chemically bonded to the polyol.

A "functional unit", as used herein, means one solvent compatibility group used to funtionalize the polyol.

"Lipophilic fluid" as used herein means any non-aqueous solvent that meets the Sebum Removal Test described hereinbelow and that is at least partially liquid and/or readily flowable (nonviscous) at ambient temperature and pressure. In general, a suitable lipophilic fluid can be fully liquid at ambient temperature and pressure, can be an easily melted solid, e.g., one which becomes liquid at temperatures in the range from about 0° C. to about 60° C., or can comprise a mixture of liquid and vapor phases at ambient temperatures and pressures, e.g., at 25° C. and 1 atm. pressure.

The present invention provides methods for administering an antimicrobial agent within a laundering device for treating fabric articles. These benefits may be delivered to the fabric article treated by the compositions of the present invention while maintaining excellent fabric care properties. It is believed that by reducing the level of the bacteria, potential odiferous compounds resulting from the metabolic activities of the microbes would be reduced. Particularly important microbes to reduce include, but are not limited to, *Bacillus*; gram positive bacteria such as *Staphylococcus aureus*; gram negative bacteria such as *Escherichia coli*; and airborne molds and fungi such as *Aspergillus niger*, and mixtures thereof.

Non-Aqueous Laundry Devices

A typical non-aqueous laundry device comprises a chamber capable of receiving a fabric article, cleaning compositions that can be added to the chamber, and a means to remove the cleaning compositions from the chamber. Suitable examples are discussed in WO 01/94675. Other suitable examples are discussed in EP 1 103 646; WO 02/08510; U.S. Pat. No. 5,940,988; U.S. Pat. No. 4,765,161; U.S. Pat. No. 5,652,194; and U.S. Pat. No. 6,346,126.

Figure 1:
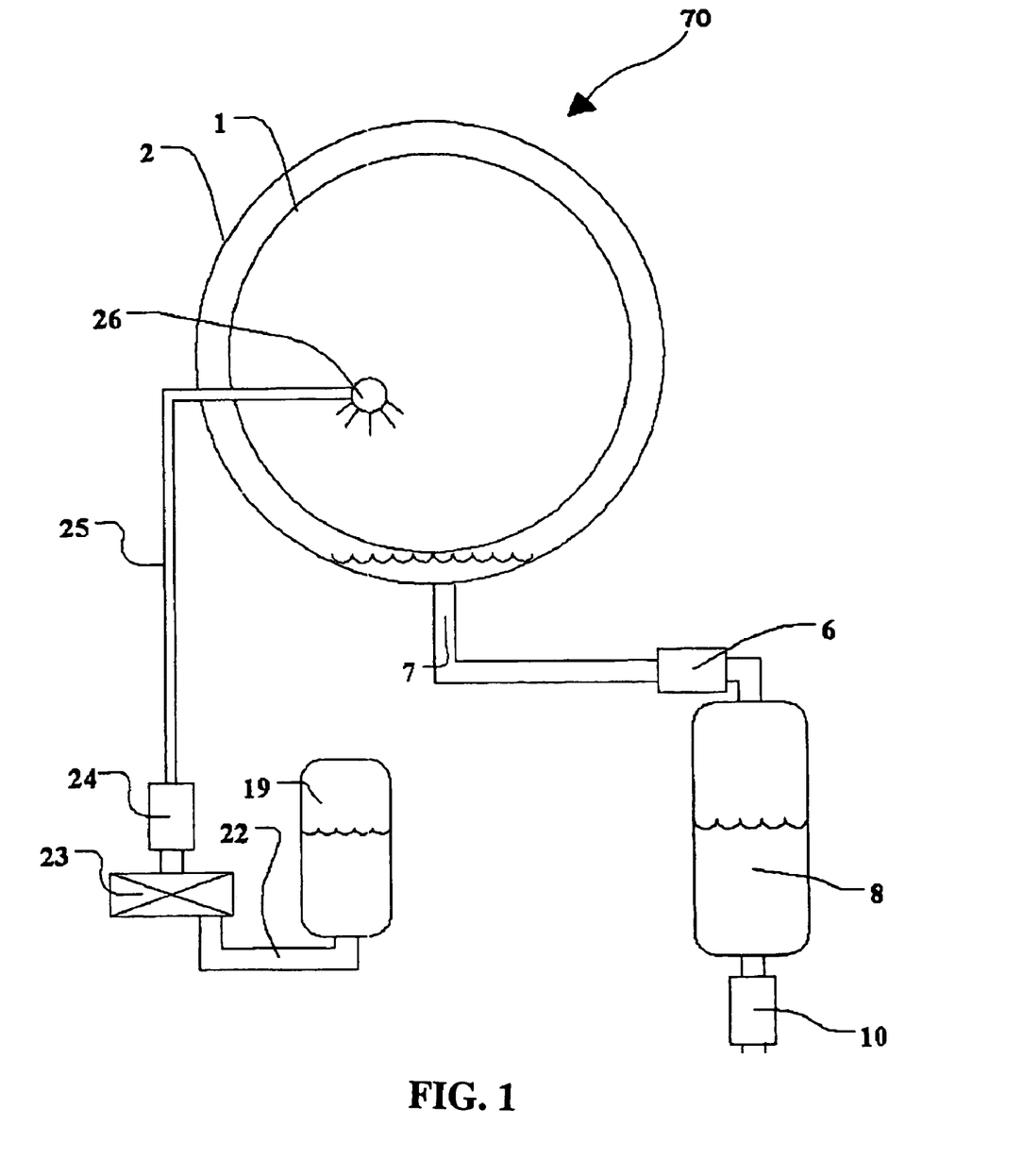
FIG. 1 illustrates a non-aqueous laundering device.
Figure 2:
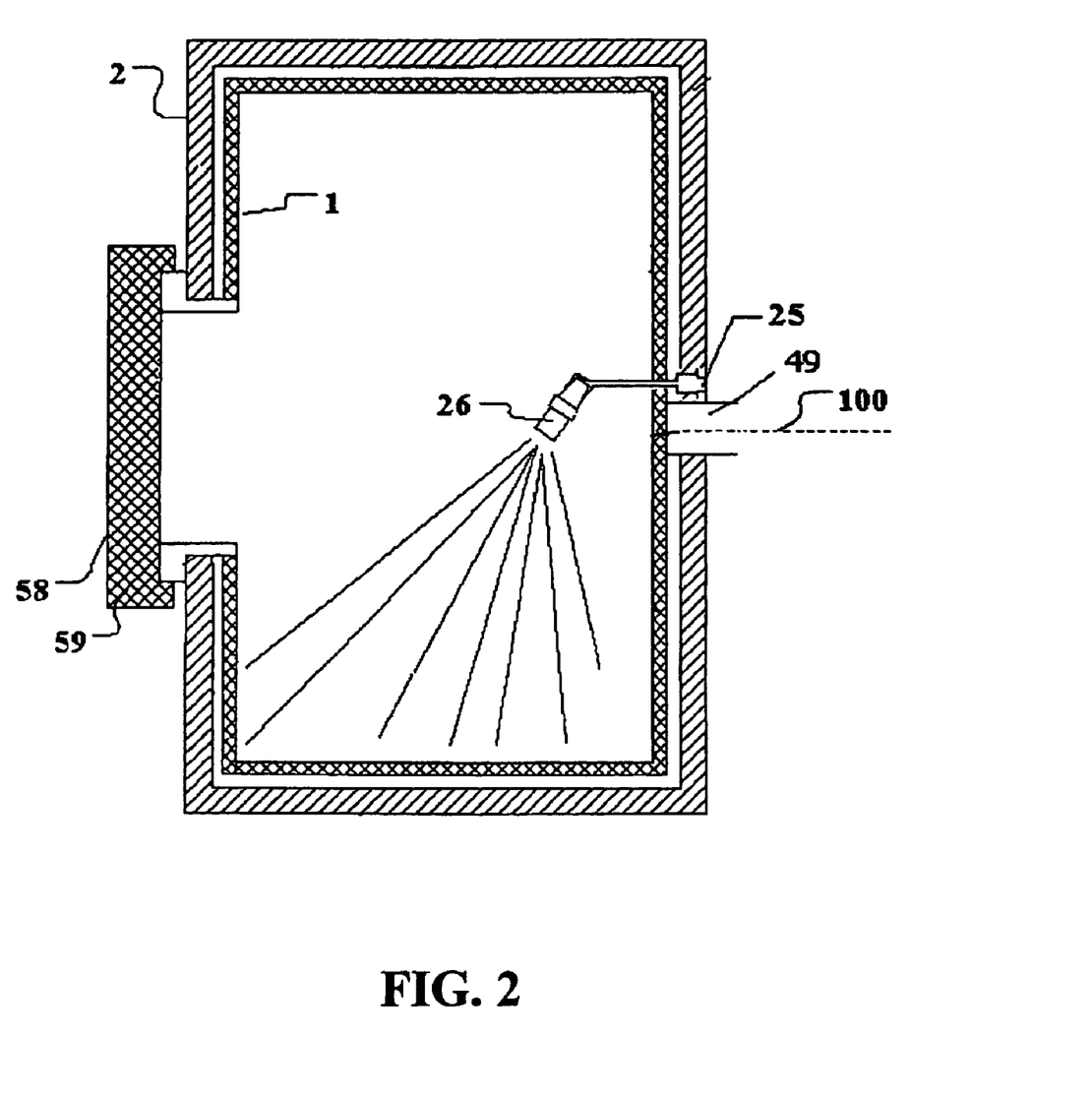
FIG. 2 further illustrates a non-aqueous laundering device.

In one embodiment of the non-aqueous laundry device 70 shown in FIG. 1, comprises a fabric-containing chamber 1 capable of receiving a fabric article to be treated and a cleaning compositon (not shown and discussed hereinbelow), wherein when a fabric article to be treated is present in the fabric-containing chamber 1, and a cleaning composition may be introduced into the fabric-containing chamber 1. The non-aqueous laundry device 70, preferably further comprises an outer chamber 2 capable of receiving the cleaning composition from the fabric-containing chamber 1 that is not retained in said fabric-containing chamber 1. The outer chamber 2 preferably houses the fabric-containing chamber 1. The fabric-containing chamber 1 and the outer chamber 2 preferably are of cylindrical construction and have a horizontal access opening 58 and 59, respectively, and, as shown in FIG. 2. The horizontal center line of the outer chamber 2, which is preferably stationary with respect to the fabric-containing chamber 1 coincides with the axis of rotation 100 of the movable fabric-containing chamber 1 movably mounted within the outer chamber 2. The outer chamber 2 preferably comprises an exit port or drain 7 through which the cleaning composition received by the outer chamber 2 exits the outer chamber 2. The fabric-containing chamber 1 is preferably rotatably secured to outer chamber 2 by means of drive shaft 49 (FIG. 2). The cross-sectional views of FIG. 2, the outer chamber 2 may have a door 59 having a circular shape with an outer edge, the door 59 is capable of opening and closing and may be used to load and unload fabric articles from the home dry cleaning system 70. The fabric-containing chamber 1 may have an access opening 58 used to load and unload fabric articles from the non-aqueous laundry device 70; preferably which is concentrically aligned with the outer edge of the door 59 in outer chamber 2. When the non-aqueous laundry device 70 is in operation, the door 59 is in the closed position, preferably locked by a locking means (not shown) when the home dry cleaning system 70 is in operation.

At least one large storage tank 19 may contain the cleaning composition. For the convenience of a user, the large storage tank 19 may optionally be detachable from the home dry cleaning system 70. The storage tank 19, may then be recycled, or can be refilled and reattached to the apparatus. Alternatively, the storage tank, 19, may be replaceable or disposable, for example as a replaceable cartridge. In one suitable mode of operation, the large storage tank 19 is recyclable, permanently fixed in the non-aqueous laundry device 70, or removable only by a trained servicer.

The desired cleaning compositions are delivered into the applicator 26 preferably by pumping with pump 24. The cleaning composition stored in the large storage tank 19 is pumped from through line 22 respectively, first passing through valve 23, then through pump 24, then finally through line 25 to applicator 26.

Once the cleaning composition enters the fabric article chamber 1, it is collected in the outer chamber 2. The cleaning composition exits the outer chamber 2 by use of a drain 7 and then enters a recover tank 8. Prior to delivering cleaning compositions into recovery tank 8, cleaning compositions are filtered in filter 6. Preferably an air compressor (not shown) would be connected to the large storage tank 19 by pressure lines. Other means of conveying home dry cleaning materials may include gravity, centrifugal, diaphragm, piston, or peristaltic pumps.

Filter 6 removes lint, fabric fibers and large particulate soil, so they don't settle on the recovery tank 8 bottom and clog downstream lines. Also, filter 6 assures reliable operation of pump 10, since pump 10 is a typically higher pressure pump which generally is of a type more easily damaged by solids.

The cleaning composition is made from various components. Such components include lipophilic fluids, surfactants, processing aids, additives, polar solvents, and cleaning adjuncts.

Lipophilic Fluid

It is preferred that the lipophilic fluid herein be nonflammable or, have relatively high flash points and/or low VOC characteristics, these terms having conventional meanings as used in the dry cleaning industry, to equal or, preferably, exceed the characteristics of known conventional dry cleaning fluids.

Sebum Removal Test

The Sebum Removal Test described herein is used to identify suitable lipophilic fluids for use in the present invention. The test method uses commercially available Crisco® canola oil, oleic acid (95% pure, available from Sigma Aldrich Co.) and squalene (99% pure, available from J. T. Baker) as model soils for sebum. The test materials should be substantially anhydrous and free from any added adjuncts, or other materials. As a general guideline, perfluorobutylamine (Fluorinert FC-43®) on its own (with or without adjuncts) is a reference material that, by definition, is unsuitable as the lipophilic fluid.

The Sebum Removal Test starts with the preparation of three vials. Place 1.0 g of canola oil in the first; in a second vial place 1.0 g of the oleic acid (95%), and in a third and final vial place 1.0 g of the squalene (99%). Add 1 g of the fluid to be tested for lipophilicity to each vial. Separately mix at room temperature and pressure each prepared vial for 20 seconds on a standard vortex mixer at maximum setting. Place vials on the bench and allow to stand for 15 minutes at room temperature and pressure. If, after 15 minutes a single phase is formed in any of the vials containing lipophilic soils, then the fluid qualifies as suitable for use as a "lipophilic fluid" in accordance with the invention. However, if two or more separate layers are formed in all three vials, then the amount of fluid dissolved in the oil phase will need to be further determined before rejecting or accepting the fluid as qualified as a "lipophilic fluid."

In such a case, with a syringe, carefully extract a 200 microliter sample from each layer in each vial. The syringe-extracted layer samples are placed in GC autosampler vials and subjected to conventional GC analysis after determining the retention time of calibration samples of each of the three models soils and the fluid being tested. If more than 1% of the test fluid by GC, preferably more, is found to be present in any one of the layers which consists of the oleic acid, canola oil or squalene layer, then the test fluid is also qualified for use as a lipophilic fluid. If needed, the method can be further calibrated using heptacosafluorotributylamine, i.e., Fluorinert FC-43 (fail) and cyclopentasiloxane (pass).

A suitable GC is a Hewlett Packard Gas Chromatograph HP5890 Series II equipped with a split/splitless injector and FID. A suitable column used in determining the amount of lipophilic fluid present is a J&W Scientific capillary column DB-1HT, 30 meter, 0.25 mm id, 0.1 um film thickness cat#1221131. The GC is suitably operated under the following conditions:

Carrier Gas: Hydrogen; Column Head Pressure: 9 psi; Flows: Column Flow @ ~1.5 ml/min.; Split Vent @ ~250-500 ml/min.; Septum Purge @ 1 mil/min.; Injection: HP 7673 Autosampler, 10 ul syringe, 1 ul injection; Injector Temperature: 350° C.; Detector Temperature: 380° C.; Oven Temperature Program: initial 60° C., hold 1 min.; rate 25° C./min.; final 380° C. hold 30 min.

Preferred lipophilic fluids suitable for use herein can further be qualified for use on the basis of having an excellent garment care profile. Garment care profile testing is well known in the art and involves testing a fluid to be qualified using a wide range of garment or fabric article components, including fabrics, threads and elastics used in seams, etc., and a range of buttons. Preferred lipophilic fluids for use herein have an excellent garment care profile; for example, they have a good shrinkage or fabric puckering profile and do not appreciably damage plastic buttons.

For purposes of garment care testing or other qualification, e.g., flammability, a lipophilic fluid for use in the lipophilic fluid can be present in a mixture, e.g., with water, at approximately the ratio to be used in the final lipophilic fluid which will come into contact with fabric articles. Certain materials, which remove sebum, qualify for use as lipophilic fluids; for example, ethyl lactates can be quite objectionable in their tendency to dissolve buttons, and if such a material is to be used in the lipophilic fluid, it will be formulated with water and/or other solvents such that the overall mix is not substantially damaging to buttons. Other lipophilic fluids, decamethyl-cyclopentasiloxane for example, meet the garment care requirements commendably. Some suitable lipophilic fluids may be found in granted U.S. Pat. Nos. 5,865,852; 5,942,007; 6,042,617; 6,042,618; 6,056,789; 6,059,845; and 6,063,135.

Nonlimiting examples of suitable lipophilic fluid materials include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

"Siloxane" as used herein means silicone fluids which are non-polar and insoluble in water or lower alcohols. Linear siloxanes (see for example U.S. Pat. Nos. 5,443,747, and 5,977,040) and cyclic siloxanes are useful herein, including the cyclic siloxanes chosen from octamethyl-cyclotetrasiloxane (tetramer), dodecamethyl-cyclohexasiloxane (hexamer), and preferably decamethyl-cyclopentasiloxane (pentamer, commonly referred to as "D5"). A preferred siloxane comprises more than about 50% cyclic siloxane pentamer, in another embodiment more than about 75% cyclic siloxane pentamer, in yet another embodiment at least about 90% of the cyclic siloxane pentamer. Also preferred for use herein are siloxanes which are a mixture of cyclic siloxanes having at least about 90% (preferably at least about 95%) pentamer and less than about 10% (preferably less than about 5%) tetramer and/or hexamer.

Mixtures of lipophilic fluid are also suitable, provided that the requirements of the Lipophilic Fluid Test, as described below, are met. The lipophilic fluid can include any fraction of dry-cleaning solvents, especially newer types including fluorinated solvents, or perfluorinated amines. Some perfluorinated amines such as perfluorotributylamines, while unsuitable for use as lipophilic fluid, may be present as one of many possible adjuncts present in the lipophilic fluid-containing composition.

Other suitable lipophilic fluids include, but are not limited to, diol solvent systems e.g., higher diols such as C6 or C8 or higher diols, organosilicone solvents including both cyclic and acyclic types, and the like, and mixtures thereof.

Nonlimiting examples of low volatility nonfluorinated organic solvents include for example OLEAN® and other polyol esters, or certain relatively nonvolatile biodegradable mid-chain branched petroleum fractions.

Nonlimiting examples of glycol ethers include propylene glycol methyl ether, propylene glycol n-propyl ether, propylene glycol t-butyl ether, propylene glycol n-butyl ether, dipropylene glycol methyl ether, dipropylene glycol n-propyl ether, dipropylene glycol t-butyl ether, dipropylene glycol n-butyl ether, tripropylene glycol methyl ether, tripropylene glycol n-propyl ether, tripropylene glycol t-butyl ether, tripropylene glycol n-butyl ether.

Nonlimiting examples of other silicone solvents, in addition to the siloxanes, are well known in the literature, see, for example, Kirk Othmer's Encyclopedia of Chemical Technology, and are available from a number of commercial sources, including GE Silicones, Toshiba Silicone, Bayer, and Dow Coming. For example, one suitable silicone solvent is SF-1528 available from GE Silicones.

Nonlimiting examples of suitable glycerine derivative solvents for use in the methods and/or apparatuses of the present invention include glycerine derivatives having the following structure:

Structure I wherein $R^1$, $R^2$ and $R^3$ are each independently selected from: Hydrogen; branched or linear, substituted or unsubstituted $C_1$-$C_{30}$ alkyl, $C_2$-$C_{30}$ alkenyl, $C_1$-$C_{30}$ alkoxycarbonyl, $C_3$-$C_{30}$ alkyleneoxyalkyl, $C_1$-$C_{30}$ acyloxy, $C_7$-$C_{30}$ alkylenearyl; $C_4$-$C_{30}$ cycloalkyl; $C_6$-$C_{30}$ aryl; mixtures thereof. Two or more of $R^1$, $R^2$ and $R^3$ together can form a $C_3$-$C_8$ aromatic or non-aromatic, heterocyclic or non-heterocyclic ring.

Nonlimiting examples of suitable glycerine derivative solvents further include 2,3-bis(1,1-dimethylethoxy)-1-propanol; 2,3-dimethoxy-1-propanol; 3-methoxy-2-cyclopentoxy-1-propanol; 3-methoxy-1-cyclopentoxy-2-propanol; carbonic acid (2-hydroxy-1-methoxymethyl)ethyl ester methyl ester; glycerol carbonate and mixtures thereof.

Nonlimiting examples of other environmentally-friendly solvents include lipophilic fluids that have an ozone reactivity of from about 0 to about 0.31, lipophilic fluids that have a vapor pressure of from about 0 to about 0.1 mm Hg, and/or lipophilic fluids that have a vapor pressure of greater than 0.1 mm Hg, but have an ozone reactivity of from about 0 to about 0.31. Nonlimiting examples of such lipophilic fluids that have not previously been described above include carbonate solvents (i.e., methyl carbonates, ethyl carbonates, ethylene carbonates, propylene carbonates, glycerine carbonates) and/or succinate solvents (i.e., dimethyl succinates).

"Ozone Reactivity" as used herein is a measure of a VOC's ability to form ozone in the atmosphere. It is measured as grams of ozone formed per gram of volatile organics. A methodology to determine ozone reactivity is discussed further in W. P. L. Carter, "Development of Ozone Reactivity Scales of Volatile Organic Compounds", Journal of the Air & Waste Management Association, Vol. 44, Page 881-899, 1994. "Vapor Pressure" as used can be measured by techniques defined in Method 310 of the California Air Resources Board.

Preferably, the lipophilic fluid comprises more than 50% by weight of the lipophilic fluid of cyclopentasiloxanes, ("D5") and/or linear analogs having approximately similar volatility, and optionally complemented by other silicone solvents.

Surfactants

The surfactant suitable for use in the present invention has the general formula:

(I)

(II)

and mixtures thereof;

wherein L and L' are solvent compatibilizing (or lipophilic) moieties, which are independently selected from:
(a) C1-C22 alkyl or C4-C12 alkoxy, linear or branched, cyclic or acyclic, saturated or unsaturated, substituted or unsubstituted;
(b) siloxanes having the formula:

wherein a is 0-2; b is 0-1000; c is 0-50; d is 0-50, provided that a+c+d is at least 1;
M is $R^1_{3-e}X_eSiO_{1/2}$ wherein $R^1$ is independently H, or an alkyl group, X is hydroxyl group, and e is 0 or 1;
D is $R^4_2SiO_{2/2}$ wherein $R^4$ is independently H or an alkyl group;
D' is $R^5_2SiO_{2/2}$ wherein $R^5$ is independently H, an alkyl group or $(CH_2)_f(C_6Q_4)_gO—(C_2H_4O)_h—(C_3H_6)_i(C_kH_{2k})_j—R^3$, provided that at least one $R^5$ is $(CH_2)_f(C_6Q_4)_gO—(C_2H_4O)_h—(C_3H_6O)_i(C_kH_{2k})_j—R^3$, wherein $R^3$ is independently H, an alkyl group or an alkoxy group, f is 1-10, g is 0 or 1, h is 1-50, i is 0-50, j is 0-50, k is 4-8; $C_6Q_4$ is unsubstituted or substituted; Q is independently selected from H, $C_{1-10}$ alkyl, $C_{2-10}$ alkenyl, and mixtures thereof; and
D'' is $R^6_2SiO_{2/2}$ wherein $R^6$ is independently H, an alkyl group or $(CH_2)_l(C_6Q_4)_{m(A)n}-[(T)_o-(A')_p-]_q-(T')_rZ(G)_s$, wherein l is 1-10; m is 0 or 1; n 0 5; is 0-3; p is 0 or 1; q is 0-10; r is 0-3; s is 0-3; $C_6Q_4$ is unsubstituted or substituted; Q is independently selected from H, $C_{1-10}$ alkyl, $C_{2-10}$ alkenyl, and mixtures thereof; A and A' are each independently a linking moiety representing an ester, a keto, an ether, a thio, an amido, an amino, a $C_{1-4}$ fluoroalkyl, a $C_{1-4}$ fluoroalkenyl, a branched or straight chained polyalkylene oxide, a phosphate, a sulfonyl, a sulfate, an ammonium, and mixtures thereof; T and T' are each independently a $C_{1-30}$ straight chained or branched alkyl or alkenyl or an aryl which is unsubstituted or substituted; Z is a hydrogen, carboxylic acid, a hydroxy, a phosphato, a phosphate ester, a sulfonyl, a sulfonate, a sulfate, a branched or straight-chained polyalkylene oxide, a nitryl, a glyceryl, an aryl unsubstituted or substituted with a $C_{1-30}$ alkyl or alkenyl, a carbohydrate unsubstituted or substituted with a $C_{1-10}$ alkyl or alkenyl or an ammonium; G is an anion or cation such as $H^+$, $Na^+$, $Li^+$, $K^+$, $NH_4^+$, $Ca^{+2}$, $Mg^{+2}$, $Cl^-$, $Br^-$, $I^-$, mesylate or tosylate; and D" can be capped with C1-C4 alkyl or hydroxy groups;

Y and Y' are hydrophilic moieties, which are independently selected from hydroxy; polyhydroxy; C1-C3 alkoxy; mono- or di- alkanolamine; C1-C4 alkyl substituted alkanolamine; substituted heterocyclic containing O, S, N; sulfates; carboxylate; carbonate; and when Y and/or Y' is ethoxy (EO) or propoxy (PO), it must be capped with R, which is selected from the group consisting of:

(i) a 4 to 8 membered, substituted or unsubstituted, heterocyclic ring containing from 1 to 3 hetero atoms; and (ii) linear or branched, saturated or unsaturated, substituted or unsubstituted, cyclic or acyclic, aliphatic or aromatic hydrocarbon radicals having from about 1 to about 30 carbon atoms;

X is a bridging linkage selected from O; S; N; P; C1 to C22 alkyl, linear or branched, saturated or unsaturated, substituted or unsubstituted, cyclic or acyclic, aliphatic or aromatic, interrupted by O, S, N, P; glycidyl, ester, amido, amino, $PO_4^{2-}$, $HPO_4^-$, $PO_3^{2-}$, $HPO_3^-$, which are protonated or unprotonated;

u and w are integers independently selected from 0 to 20, provided that $u+w \geq 1$;

t is an integer from 1 to 10;

v is an integer from 0 to 10;

x is an integer from 1 to 20; and y and z are integers independently selected from 1 to 10.

Nonlimiting examples of surfactants having the above formula include:

(1) alkanolamines;

(2) phophate/phosphonate esters;

(3) gemini surfactants including, but are not limited to, gemini diols, gemini amide alkoxylates, gemini amino alkoxylates;

(4) capped nonionic surfactants;

(5) capped silicone surfactants such as nonionic silicone ethoxylates, silicone amine derivatives;

(6) alkyl alkoxylates;

(7) polyol surfactants; and mixtures thereof.

Another class of surfactant can include siloxane-based surfactants. The siloxane-based surfactants in this application may be siloxane polymers for other applications. The siloxane-based surfactants typically have a weight average molecular weight from 500 to 20,000 daltons. Such materials, derived from poly(dimethylsiloxane), are well known in the art. In the present invention, not all such siloxane-based surfactants are suitable, because they do not provide improved cleaning of soils compared to the level of cleaning provided by the lipophilic fluid itself.

Suitable siloxane-based surfactants comprise a polyether siloxane having the formula:

$$M_a D_b D'_c D''_d M'_{2-a}$$

wherein a is 0-2; b is 0-1000; c is 0-50; d is 0-50, provided that a+c+d is at least 1;

M is $R^1_{3-e}X_e SiO_{1/2}$ wherein $R^1$ is independently H, or a monovalent hydrocarbon group, X is hydroxyl group, and e is 0 or 1;

M' is $R^2_3 SiO_{1/2}$ wherein $R^2$ is independently H, a monovalent hydrocarbon group, or $(CH_2)_f(C_6Q_4)_g O—(C_2H_4O)_h—(C_3H_6O)_i(C_kH_{2k})_j—R^3$, provided that at least one $R^2$ is $(CH_2)_f(C_6Q_4)_g O—(C_2H_4O)_h—(C_3H_6O)_i(C_kH_{2k})_j—R^3$, wherein $R^3$ is independently H, a monovalent hydrocarbon group or an alkoxy group, f is 1-10, g is 0 or 1, h is 1-50, i is 0-50, j is 0-50, k is 4-8; $C_6Q_4$ is unsubstituted or substituted; Q is independently selected from H, $C_{1-10}$ alkyl, $C_{1-10}$ alkenyl, and mixtures thereof;

D is $R^4_2 SiO_{2/2}$ wherein $R^4$ is independently H or a monovalent hydrocarbon group;

D' is $R^5_2 SiO_{2/2}$ wherein $R^5$ is independently $R^2$ provided that at least one $R^5$ is $(CH^2)_f(C_6Q_4)_g O—(C_2H_4O)_h—(C_3H_6O)_i(C_kH_{2k})_j—R^3$ is independently H, a monovalent hydrocarbon group or an alkoxy group, f is 1-10, g is 0 or 1, h is 1-50, i is 0-50, j is 0-50, k is 4-8; $C_6Q_4$ is unsubstituted or substituted; Q is independently selected from H, $C_{1-10}$ alkyl, $C_{1-10}$ alkenyl, and mixtures thereof; and D" is $R^6_2 SiO_{2/2}$ wherein $R^6$ is independently H, a monovalent hydrocarbon group or $(CH_2)_f(C_6Q_4)_m(A)_n-[(L)_o-(A')_p-]_q-(L')_r Z(G)_s$, wherein l is 1-10; m is 0 or 1; n is 0-5; o is 0-3; p is 0 or 1; q is 0-10; r is 0-3; s is 0-3; $C_6Q_4$ is unsubstituted or substituted; Q is independently a selected from H, $C_{1-10}$ alkyl, $C_{1-10}$ alkenyl, and mixtures thereof; A and A' are each independently a linking moiety representing an ester, a keto, an ether, a thio, an amido, an amino, a $C_{1-4}$ fluoroalkyl, a $C_{1-4}$ fluoroalkenyl, a branched or straight chained polyalkylene oxide, a phosphate, a sulfonyl, a sulfate, an ammonium, and mixtures thereof; L and L' are each independently a $C_{1-30}$ straight chained or branched alkyl or alkenyl or an aryl which is unsubstituted or substituted; Z is a hydrogen, carboxylic acid, a hydroxy, a phosphato, a phosphate ester, a sulfonyl, a sulfonate, a sulfate, a branched or straight-chained polyalkylene oxide, a nitryl, a glyceryl, an aryl unsubstituted or substituted with a $C_{1-30}$ alkyl or alkenyl, a carbohydrate unsubstituted or substituted with a $C_{1-10}$ alkyl or alkenyl or an ammonium; G is an anion or cation such as $H^+$, $Na^+$, $Li^+$, $K^+$, $NH_4^+$, $Ca^{+2}$, $Mg^{+2}$, $Cl^-$, $Br^-$, $I^-$, mesylate or tosylate.

Examples of the types of siloxane-based surfactants described herein above may be found in EP-1,043,443A1, EP-1,041,189 and WO-01/34,706 (all to GE Silicones) and U.S. Pat. No. 5,676,705, U.S. Pat. No. 5,683,977, U.S. Pat. No. 5,683,473, and EP-1,092,803A1 (all assigned to Lever Brothers).

Nonlimiting commercially available examples of suitable siloxane-based surfactants are TSF 4446 (ex. General Electric Silicones), XS69-B5476 (ex. General Electric Silicones); Jenamine HSX (ex. DelCon) and Y12147 (ex. OSi Specialties).

Yet another preferred class of materials suitable for the surfactant component is organic in nature. Preferred materials are organosulfosuccinate surfactants, with carbon chains of from about 6 to about 20 carbon atoms. Most preferred are organosulfosuccinates containing dialkly chains, each with carbon chains of from about 6 to about 20 carbon atoms. Also preferred are chains containing aryl or alkyl aryl, substituted or unsubstituted, branched or linear, saturated or unsaturated groups. Nonlimiting commercially available examples of suitable organosulfosuccinate surfactants are available under the trade names of Aerosol OT and Aerosol TR-70 (ex. Cytec).

The surfactant component, when present in the compositions of the present invention, preferably comprises from about 1% to about 99%, more preferably 2% to about 75%, even more preferably from about 5% to about 60% by weight of the composition.

When the composition is diluted with a lipophilic fluid to prepare the wash liquor, the surfactant component preferably comprises from about 0.01% to about 10%, more preferably from about 0.02% to about 5%, even more preferably from about 0.05% to about 2% by weight of the wash liquor.

Non-Silicone Additive

The optional non-silicone additive (i.e., materials do not contain an Si atom), which preferably comprises a strongly polar and/or hydrogen-bonding head group, further enhances soil removal by the compositions of the present invention. Examples of the strongly polar and/or hydrogen-bonding head group-containing materials include, but are not limited to alcohols, cationic materials such as cationic surfactants, quaternary surfactants, quaternary ammonium salts such as ammonium chlorides (nonlimiting examples of ammonium chlorides are Arquad materials commercially available from Akzo Nobel) and cationic fabric softening actives, nonionic materials such as nonionic surfactants (i.e., alcohol ethoxylates, polyhydroxy fatty acid amides), gemini surfactants, anionic surfactants, zwitterionic surfactants, carboxylic acids, sulfates, sulphonates, phosphates, phosphonates, and nitrogen containing materials. In one embodiment, non-silicone additives comprise nitrogen containing materials chosen from primary, secondary and tertiary amines, diamines, triamines, ethoxylated amines, amine oxides, amides and betaines, a nonlimiting example of a betaines is Schercotaine materials commercially available from Scher Chemicals and mixtures thereof.

In another embodiment embodiment, alkyl chain contains branching that may help lower the melting point.

In yet another embodiment, primary alkylamines comprising from about 6 to about 22 carbon atoms are used. Particularly preferred primary alkylamines are oleylamine (commercially available from Akzo under the trade name Armeen OLD), dodecylamine (commercially available from Akzo under the trade name Armeen 12D), branched $C_{16}$-$C_{22}$ alkylamine (commercially available from Rohm & Haas under the trade name Primene JM-T) and mixtures thereof.

Suitable cationic materials may include quaternary surfactants, which maybe quaternary ammonium compounds. Commercially available agents include Varisoft materials from Goldschmidt.

Polar Solvent

Compositions according to the present invention may further comprise a polar solvent. Non-limiting examples of polar solvents include: water, alcohols, glycols, polyglycols, ethers, carbonates, dibasic esters, ketones, other oxygenated solvents, and mixtures thereof. Further examples of alcohols include: $C_1$-$C_{126}$ alcohols, such as propanol, ethanol, isopropyl alcohol, etc . . . , benzyl alcohol, and diols such as 1,2-hexanediol. The Dowanol series by Dow Chemical are examples of glycols and polyglycols useful in the present invention, such as Dowanol TPM, TPnP, DPnB, DPnP, TPnB, PPh, DPM, DPMA, DB, and others. Further examples include propylene glycol, butylene glycol, polybutylene glycol and more hydrophobic glycols. Examples of carbonate solvents are ethylene, propylene and butylene carbonantes such as those available under the Jeffsol tradename. Polar solvents for the present invention can be further identified through their dispersive ($\delta_D$), polar ($\delta_P$) and hydrogen bonding ($\delta_H$) Hansen solubility parameters. Preferred polar solvents or polar solvent mixtures have fractional polar ($f_P$) and fractional hydrogen bonding ($f_H$) values of $f_P$>0.02 and $f_H$>0.10, where $f_P = \delta_P/(\delta_D+\delta_P+\delta_H)$ and $f_H = \delta_H/(\delta_D+\delta_P+\delta_H)$, more preferably $f_P$>0.05 and $f_H$>0.20, and most preferably $f_P$>0.07 and $f_H$>0.30.

In the detergent composition of the present invention, the levels of polar solvent can be from about 0 to about 70%, preferably 1 to 50%, even more preferably 1 to 30% by weight of the detergent composition.

Water, when present in the wash fluid fabric article treating compositions of the present invention, the wash fluid composition may comprise from about 0.001% to about 10%, more preferably from about 0.005% to about 5%, even more preferably from about 0.01% to about 1% by weight of the wash fluid fabric article treating composition.

Water, when present in the detergent compositions of the present invention, preferably comprises from about 1% to about 90%, more preferably from about 2% to about 75%, even more preferably from about 5% to about 40% by weight of the consumable detergent composition.

Processing Aids

Optionally, the compositions of the present invention may further comprise processing aids. Processing aids facilitate the formation of the fabric article treating compositions of the present invention, by maintaining the fluidity and/or homogeneity of the consumable detergent composition, and/or aiding in the dilution process. Processing aids suitable for the present invention are solvents, preferably solvents other than those described above, hydrotropes, and/or surfactants, preferably surfactants other than those described above with respect to the surfactant component. Particularly preferred processing aids are protic solvents such as aliphatic alcohols, diols, triols, etc. and nonionic surfactants such as ethoxylated fatty alcohols.

Processing aids, when present in the fabric article treating compositions of the present invention, preferably comprise from about 0.02% to about 10%, more preferably from about 0.05% to about 10%, even more preferably from about 0.1% to about 10% by weight of the fabric article treating composition.

Processing aids, when present in the consumable detergent compositions of the present invention, preferably comprise from about 1% to about 75%, more preferably from about 5% to about 50% by weight of the consumable detergent composition.

Cleaning Adjuncts

Some suitable cleaning adjuncts include, but are not limited to, builders, surfactants, other than those described above with respect to the surfactant component, enzymes, bleach activators, bleach catalysts, bleach boosters, bleaches, alkalinity sources, antibacterial agents, colorants, perfumes, pro-perfumes, finishing aids, lime soap dispersants, odor control agents, odor neutralizers, polymeric dye transfer inhibiting agents, crystal growth inhibitors, photobleaches, heavy metal ion sequestrants, anti-tarnishing agents, anti-microbial agents, anti-oxidants, anti-redeposition agents, soil release polymers, electrolytes, pH modifiers, thickeners, abrasives, divalent or trivalent ions, metal ion salts, enzyme stabilizers, corrosion inhibitors, polyamines and/or their alkoxylates, suds stabilizing polymers, solvents, process aids, fabric softening agents, optical brighteners, hydrotropes, suds or foam suppressors, suds or foam boosters and mixtures thereof.

Antimicrobial Agent in Filter

In one embodiment, the antimicrobial agent of the present invention is utilized with a filter of the laundering device. The antimicrobial agent can be utilized with the filter by several methods. In a preferred embodiment, the antimicrobial agent is coated onto the filter. In a more preferred embodiment embodiment, the antimicrobial agent is embedded within the filter.

Any antimicrobial agent that can be embedded or coated onto the filter can be used. Preferred antimicrobial agent for filter are zinc oxide, and metal particulates, such as colloidal gold or silver.

The filter of this embodiment has a pore size (0.1-100 µm), such that the bulk solvent would pass through the filter, leaving behind a small amount of bulk solvent or water with the microbes concentrated in that solution. The microbes in that solution that come in contact with the antimicrobial agents on the filter are destroyed or their metabolic activities are minimized.

Contacting Antimicrobial Agent with Lipophilic Fluid

Antimicrobial agents can be contacted with the lipophilic fluid of the present invention. Any antimicrobial agent capable of reducing the level of microbes within the compositions of the present invention can be utilized. The preferred level of antimicrobial agent is 0.001-20% by weight. The most preferred level is 0.01-1.0%.

Any method of delivering the antimicrobial agent to the lipophilic fluid can be utilized. In one preferred method, the antimicrobial agent is solubilized prior to contacting the lipophilic fluid. In another preferred method an insoluble antimicrobial agent in the form of particulates, are delivered to the lipophilic fluid. In another preferred method, the antimicrobial agents are bound to a solid surface, such as a filter or column and the fluid containing the microbes is passed through the substrate or column. The exiting fluid should have the microbes reduced by 0.5 log, preferably 1.0 log.

Antimicrobial agents of the present invention preferably comprise from about 0.0001% to about 20%, even more preferably from about 0.01% to about 1.0%.

Another method of contacting the lipophilic fluid with an antimicrobial agent where the lipophilic fluid is contacted with one of the preferred classes of antimicrobial agents or an antimicrobial in vapor phase. A preferred antimicrobial in vapor phase is ozone. Another preferred antimicrobial in vapor phase is formaldehyde. The antimicrobial agents would be added to the lipophilic fluid for a long enough time period in order to affect antimicrobial activity. Optionally, the lipophilic is then filtered to remove microbes and microbial fragments that have been destroyed.

Antimicrobial Contacted to Fabric Articles

In another embodiment, the antimicrobial agent is contacted directly to the fabric articles. This contacting can occur at any point during the laundering process. In one embodiment, the antimicrobial agent is contacted with the fabric articles before the laundering process. In another embodiment, the antimicrobial agent is contacted with the fabric articles during the laundering process. In yet another embodiment, the antimicrobial agent is contacted with the fabric articles after the laundering process. In yet another embodiment, the antimicrobial agent is delivered during the drying process to the fabric articles.

Antimicrobial Agents

Various antimicrobial agents can be used in the methods and compositions of the present invention. Any antimicrobial agent capable of reducing the level of microbes within the compositions of the present invention can be utilized. It is believed that by reducing the level of the bacteria, potential odiferous compounds resulting from the metabolic activities of the microbes would be reduced. Particularly important microbes to reduce include, but are not limited to, *Bacillus*; gram positive bacteria such as *Staphylococcus aureus*; gram negative bacteria such as *Escherichia coli*; and airborne molds and fungi such as *Aspergillus niger*, and mixtures thereof. One of ordinary skill in the art would readily be able to select an appropriate antimicrobial agent.

Any antimicrobial agent suitable for fabric care can be used. Such antimicrobial agents include, but are not limited to the following: Acetylsalicylic acid, n-Alkyl (68% C12, 32% C14) dimethyl dimethylbenzyl ammonium, amine acetate, amine hydrochloride, 1-(Alkyl, amino)-3-aminopropane, 1-(Alkyl, amino)-3-aminopropane, 1-(Alkyl, amino)-3-aminopropane diacetate, 1-(Alkyl, amino)-3-aminopropane hydroxyacetate, (1-(Alkyl, amino)-3-aminopropane monoacetate, Alkyl, dimethyl 1-naphthylmethyl ammonium, dimethyl benzyl ammonium chloride, dimethyl benzyl ammonium, dimethyl benzyl ammonium saccharinate, dimethyl dimethylbenzyl ammonium chloride, dimethyl ethyl ammonium bromide, dimethyl ethylbenzyl ammonium chloride, alpha-Alkyl-omega-hydroxypoly(oxyethylene)-iodine complex, 4-tert-Amylphenol, p-tert-Amylphenol, potassium salt, p-tert-Amylphenol, sodium salt, Barium metaborate, Basic copper chloride, 1,2-Benzenedicarboxaldehyde, 1,2-Benzisothiazolin-3-one, 2-Benzyl-4-chlorophenol, 1,4-Bis(bromoacetoxy)-2-butene, Bis(tributyltin) oxide, Bis(trichloromethyl), sulfone, Borax (B4Na2O7.10H2O) (1303-96-4), Boric acid, Boron sodium oxide (B4Na2O7), pentahydrate, Boron sodium oxide (B8Na2O13), tetrahydrate (12280-03-4), Bromine, Bromine chloride, 1-Bromo-1-(bromomethyl)-1,3-propanedicarbonitrile, 2-Bromo-2-nitropropane-1,3-diol, 1-Bromo-3-chloro-5,5-dimethylhydantoin, 2-Bromo-4'-hydroxyacetophenone, beta-Bromo-beta-nitrostyrene, 1-Butanethiol, Butoxypolypropoxypolyethoxyethanol-iodine complex, 2-tert-Butylamino-4-chloro-6-ethylamino-s-triazine, (Butylcarbityl) (6-propylpiperonyl) ether 80% and related comp, Calcium hypochlorite, Capric acid, Caprylic acid, Chlorhexidine diacetate, Chlorinated trisodium phosphate, Chlorine, Chlorine dioxide, 5-Chloro-2-(2,4-dichlorophenoxy)phenol, 5-Chloro-2-methyl-3-(2H)-isothiazolone, (Z)-1-(3-Chloro-2-propenyl)-3,5,7-triaza-1-azoniatricyclo(3.3, 4-Chloro-3,5-xylenol, 4-Chloro-3-cresol, 1-(3-Chloroallyl)-3,5,7-triaza-1-azoniaadamantane chloride, Chromic acid, Citric acid, Copper (metallic), Copper oxychloride (Cu2Cl(OH)3), Copper sulfate, Creosote oil, Cupric oxide, Cuprous oxide, Decyl isononyl dimethyl ammonium chloride, 2-(Decylthio) ethanamine hydrochloride, Dialkyl, methyl benzyl ammonium chloride, (60% C14, 30% C16, 2,2-Dibromo-3-nitrilopropionamide, 1,3-Dibromo-5,5-dimethylhydantoin, 4,5-Dichloro-2-n-octyl-3(2H)-isothiazolone, 1,3-Dichloro-5,5-dimethylhydantoin, 1,3-Dichloro-5-ethyl-5-methylhydantoin, Dichloro-s-triazinetrione, 1-((2-(2,4-Dichlorophenyl)-4-propyl-1,3-dioxolan-2-yl)methyl), Didecyl dimethyl ammonium chloride, N,N-Didecyl-N-methyl-3-(trimethoxysilyl)propanaminium chlorid, Dihydro-5-pentyl-2(3H)-furanone, Diiodomethyl p-tolyl sulfone, Diisobutylcresoxyethoxyethyl dimethyl benzyl ammonium chlorid, Diisobutylphenoxyethoxyethyl dimethyl benzyl ammonium chlorid, Dimethyl phthalate, 2,6-Dimethyl-m-dioxan-4-ol acetate, 1,3-Dimethylol-5,5-dimethylhydantoin, 4,4-Dimethyloxazolidine, Dioctyl dimethyl ammonium chloride, Disodium, anodithioimidocarbonate, Disodium ethylenebis(dithiocarbamate), 3H-1,2-Dithiol-3-one, 4,5-dichloro-Dodecyl bis(2-hydroxyethyl) octyl hydrogen ammonium phosphate, Dodecyl bis(hydroxyethyl)dioctyl ammonium phosphate, Dodecylbenzenesulfonic acid, Dodecylguanidine acetate, Dodecylguanidine hydrochloride, Ethanol, Ethyl sulfide, 4,4'-(2-Ethyl-2-nitrotrimethylene)dimorpholine, 7a-Ethyldihydro-1H,3H,5H-oxazolo(3,4-c)oxazole, Ethylene oxide, Ethylenediaminetetraacetic acid, Formaldehyde, Glutaraldehyde, 5-Heptyldihydro-2(3H-furanone, Hexahydro-1,3,5-tris(2-hydroxyethyl)-s-triazine, Hydrogen chloride (hydrochloric acid, anhydrous), Hydrogen peroxide, 1-Hydroxy-2-(1H)-pyridinethione, sodium salt, 1-(2-Hydroxyethyl)-2-alkyl-2-imidazoline (as in fatty acids o, 5-Hydroxymethoxymethyl-1-aza-3,7-dioxabicyclo (3.3.0)octane, 2-(Hydroxymethyl)-2-nitro-1,3-propanediol, 2-((Hydroxymethyl)amino)-2-methyl-1-propanol, 2-((Hydroxymethyl)amino)ethanol, 5-Hydroxymethyl-1-aza-3,7-dioxabicyclo(3.3.0)octane, 5-Hydroxypoly(methyleneoxy)* methyl-1-aza-3,7-dioxabicyclo(3, S-(2-Hydroxypropyl) thiomethanesulfonate, 5-Hydroxytetracycline monohydrochloride, Iodine, Iodine-potassium iodide complex, 3-Iodo-2-propynyl butylcarbamate, Isopropanol, L-Lactic acid, Limonene, Lithium hypochlorite, Manganese ethylenebis (dithiocarbamate), 2-Mercaptobenzothiazole, sodium salt, 2-Mercaptobenzothiazole, zinc salt, Methanol, (((2-(dihydro-5-methyl-3(2H)-oxazolyl)-1-methyl)eth, Methyl alcohol, Methyl bromide, Methyl salicylate, 2-Methyl-3(2H)-isothiazolone, 2-Methyl-4,5-trimethylene-4-isothiazolin-3-one, 2-Methyl-4-oxo-3-(2-propenyl)-2-cyclopenten-1-yl 2,2-dimethyl, Methyldodecylbenzyl trimethyl ammonium chloride 80% and methyl, Methylenebis(thiocyanate), 2,2'-(1-Methyltrimethylenedioxy)bis(4-methyl-1,3,2-dioxaborin, Monomethylol-5,5-dimethylhydantoin, Nitrilotriacetic acid, trisodium salt, 4-(2-Nitrobutyl)morpholine, Nonanoic acid, Nonylphenoxypolyethoxyethanol-iodine complex, N-Octyl bicycloheptene dicarboximide, Octyl decyl dimethyl ammonium chloride, 2-Octyl-3(2H)-isothiazolone, jasmine, 7-Oxabicyclo(2.2.1)heptane-2,3-dicarboxylic acid, 2,2'-Oxybis(4,4,6-trimethyl-1,3,2-dioxaborinane), 10,10'-Oxybisphenoxarsine, Oxydiethylenebis(alkyl* dimethyl ammonium chloride), Paradichlorobenzene, Paraformaldehyde, Peroxyacetic acid, Phenol, (3-Phenoxyphenyl)methyl d-cis and trans, 2,2-dimethyl-3-(2-me, o-Phenylphenol, o-Phenylphenol, potassium salt, Phosphoric acid, Phosphoric acid, bis(2-ethylhexyl) ester, compd. with 2,2'-(c, Phosphoric acid, mono(2-ethylhexyl) ester, Phosphoric acid, mono(2-ethylhexyl) ester, Pine oil, Poly (iminoimidocarbonyliminoimi-docarbonyliminohexamethylene), poly(oxyethylene(dimethyliminio)ethylene(dimethyliminio)ethyl, Polyethoxypolypropoxyethanol—iodine complex, Polyvinylpyrrolidone—iodine complex, Potassium 2-benzyl-4-chlorophenate, Potassium N-hydroxymethyl-N-methyldithiocarbamate, Potassium N-methyldithiocarbamate, Potassium cresylate, Potassium dimethyldithiocarbamate, Potassium iodide, Potassium permanganate, Potassium peroxymonosulfate, Potassium salts of fatty acids, 1,2-Propanediol, Propanol, oxybis-, 2-Propenal, Propionic acid, Propylene oxide, Pseudomonas Syringae 742RS, Pseudomonas fluorescens 1629RS, Pseudomonas fluorescens A506 (previously coded 006418), Putrescent whole egg solids, 1H-Pyrazole-1-methanol, 3,5-dimethyl-(9CI), Pyrethrins, 1H-Pyrrole-3-carbonitrile, 4-(2,2-difluoro-1,3-benzodioxol-4-, Silver, Silver nitrate, Silver oxide, Soap, Sodium 2-benzyl-4-chlorophenate, Sodium N-methyldithiocarbamate, Sodium bisulfate, Sodium bromide, Sodium carbonate, Sodium chlorate, Sodium chloride, Sodium chlorite, Sodium dichloro-s-triazinetrione, Sodium dichloroisocyanurate dihydrate, Sodium dimethyldithiocarbamate, Sodium dodecylbenzenesulfonate, Sodium hypochlorite, Sodium metasilicate, Sodium o-phenylphenate, Sodium perborate monohydrate, Sodium phenate, Sodium tetrahydro-3,5-dimethyl-2H-1,3,5-thiadiazine-2-thione, Streptomycin sulfate, Sulfonated oleic acid, sodium salt, Sulfuric acid, Tetrachloroisophthalonitrile, Tetraglycine hydroperiodide, Tetrahydro-3,5-dimethyl-2H-1,3,5-thiadiazine-2-thione, Tetrakis(hydroxymethyl)phosphonium sulphate (THPS), Tetrasodium, thylenediaminetetraacetate, 2-(4'-Thiazolyl)benzimidazole, 2 Thiocyanomethylthio)benzothiazole, Thymol, 3,5,7 Triazazoniatricyclo (3.3.1.1 (superscript3,7))decane, Tributyltin benzoate, Tributyltin maleate, Trichloro-s-triazinetrione, Trichloromelamine, cis-N-Trichloromethylthio-4-cyclohexene-1,2-dicarboximide, Triethanolamine dodecylbenzenesulfonate, Triethylene glycol, 1,3,5-Triethylhexahydro-s-triazine, 3-(Trimethoxysilyl)propyl dimethyl octadecyl ammonium chlorid, Tris(2-hydroxyethyl)amine, Trisodium (2-hydroxyethyl)ethylenediaminetriacetate, Trisodium phosphate, Zinc, Zinc 2-pyridinethiol-1-oxide, Zinc dimethyldithiocarbamate, Zinc oxide, and mixtures thereof.

Preferred antimicorbial agents are o-phenylphenol, Bromonitropropane diol (Bronopol), Tris (hydroxymethyl)nitromethane, Silicone Quaternary Ammonium salt (Octadecylaminodimethyltrimethoxysilylpropyl ammonium chloride), Silver Zeolite, Benzoimidazole, 2-(4-thiazolyl), Hinokitiol, Propenenitriles, Triclosan (2,4,4'-trichloro-2' hydroxy diphenyl-ether, Cyclopropyl-N'-(1,1-dimethylethyl)-6-(methylthio)-1,3,5-triazine-2,4-diamine, Zinc Oxide, Benzimidazole, 2-(4-Thiazolyl)-2,6-Dimethyl-1,3-dioxan-4-ol acetate, 1-Aza-3,7-dioxa-5-ethyl-bicyclo-(3,3,0)-octane, 2-Bromo-2-nitro-1,3-propanediol, 2-(hydroxy methyl)-2-nitro-1,3-propanediol, Propanediamide, 2,2-dibromo-2,4,4'-Trichloro-2-hydroxydiphenyl ether, 4,4'-Dichloro-2-hydroxydiphenyl ether, Tetrakis(hydroxymethyl)phosphonium sulfate, and mixtures thereof.

What is claimed is:

1. A method of treating microbes in a non-aqueous laundering process comprising
    a) Laundering fabric articles by a non-aqueous laundering process using a cleaning composition comprising decamethylcyclopentasiloxane,
    b) Introducing 4'-Dichloro-2-hydroxydiphenyl ether antimicrobial agent to the cleaning composition used in step (a), by passing said cleaning composition through a filter having a pore size of 0.1-100 μm and having said antimicrobial agent coated on or embedded within said filter,
  thereby reducing the effectiveness of the microbes with the antimicrobial agent, and
    c) Optionally removing the microbes.

* * * * *

UNITED STATES PATENT AND TRADEMARK OFFICE
CERTIFICATE OF CORRECTION

PATENT NO. : 7,259,133 B2 Page 1 of 1
APPLICATION NO. : 10/877549
DATED : August 21, 2007
INVENTOR(S) : Chanchal Kumar Ghosh et al.

It is certified that error appears in the above-identified patent and that said Letters Patent is hereby corrected as shown below:

<u>Column 6</u>

Line 17, delete "mil/min." and insert -- ml/min. --.

<u>Column 7</u>

Line 5 after Structure I, insert -- and -- in front of mixtures thereof.

Line 35, delete "Coming" and insert -- Corning --.

<u>Column 8</u>

Line 42, delete "$(C_3H_6)_i$;" and insert -- $(C_3H_6O)_i$ --.

Signed and Sealed this

Fifteenth Day of April, 2008

JON W. DUDAS
*Director of the United States Patent and Trademark Office*